(12) United States Patent
Booker et al.

(10) Patent No.: US 12,263,047 B2
(45) Date of Patent: Apr. 1, 2025

(54) INTRAVASCULAR DATA COLLECTION PROBES AND RELATED ASSEMBLIES

(71) Applicant: LightLab Imaging, Inc., Westford, MA (US)

(72) Inventors: James Booker, Leominster, MA (US); David Ellman, Littleton, MA (US); Douglas Tatosian, West Boylston, MA (US); Charles Milne, Hudson, MA (US)

(73) Assignee: LightLab Imaging, Inc., Westford, MA (US)

(*) Notice: Subject to any disclaimer, the term of this patent is extended or adjusted under 35 U.S.C. 154(b) by 0 days.

(21) Appl. No.: 18/243,924

(22) Filed: Sep. 8, 2023

(65) Prior Publication Data
US 2023/0414314 A1  Dec. 28, 2023

Related U.S. Application Data

(63) Continuation of application No. 17/750,978, filed on May 23, 2022, now Pat. No. 12,036,074, which is a
(Continued)

(51) Int. Cl.
*A61B 5/00* (2006.01)
*A61B 90/00* (2016.01)

(52) U.S. Cl.
CPC ............ *A61B 90/39* (2016.02); *A61B 5/0066* (2013.01); *A61B 5/0084* (2013.01); *A61B 2090/3966* (2016.02)

(58) Field of Classification Search
CPC ..... A61B 90/39; A61B 5/0066; A61B 5/0084; A61B 2090/3966
See application file for complete search history.

(56) References Cited

U.S. PATENT DOCUMENTS 4,648,892 A * 3/1987 Kittrell ................ A61B 18/245
                                                    606/7
4,666,238 A * 5/1987 Borsuk ................ G02B 6/3838
                                                    385/83
(Continued)

FOREIGN PATENT DOCUMENTS

CN    108463176 A    8/2018
CN    111225622 A    6/2020
(Continued)

OTHER PUBLICATIONS

Extended European Search Report issued in Appln. No. 22185311.2 dated Oct. 28, 2022 (6 pages).
(Continued)

*Primary Examiner* — Peter Radkowski
(74) *Attorney, Agent, or Firm* — Lerner David LLP

(57) ABSTRACT

In one embodiment, the disclosure relates to a probe that a cylindrical marker band defining an inner surface, an outer surface, a first end and a second end and having a band length, the inner surface defining a marker band bore, the cylindrical marker band includes a radiopaque material; a molded unitary lens defining an elongate optical fiber receiving section having a fiber section length and a beam directing surface, wherein the fiber section length and the band length overlap along an overlap distance; and an optical fiber, wherein a first section of the optical fiber is disposed in the optical fiber receiving section, wherein a portion of the first section of the optical fiber is disposed within the marker band bore.

20 Claims, 10 Drawing Sheets

Related U.S. Application Data continuation of application No. 16/149,886, filed on Oct. 2, 2018, now abandoned.

(60) Provisional application No. 62/567,189, filed on Oct. 2, 2017.

(56) References Cited

U.S. PATENT DOCUMENTS

| | | | |
|---|---|---|---|
| 4,958,634 A | 9/1990 | Jang | |
| 5,321,501 A | 6/1994 | Swanson et al. | |
| 5,459,570 A | 10/1995 | Swanson et al. | |
| 5,465,147 A | 11/1995 | Swanson | |
| 5,509,093 A | 4/1996 | Miller et al. | |
| 5,619,368 A | 4/1997 | Swanson | |
| 5,748,598 A | 5/1998 | Swanson et al. | |
| 5,784,352 A | 7/1998 | Swanson et al. | |
| 5,956,355 A | 9/1999 | Swanson et al. | |
| 6,111,645 A | 8/2000 | Tearney et al. | |
| 6,134,003 A | 10/2000 | Tearney et al. | |
| 6,160,826 A | 12/2000 | Swanson et al. | |
| 6,191,862 B1 | 2/2001 | Swanson et al. | |
| 6,282,011 B1 | 8/2001 | Tearney et al. | |
| 6,421,164 B2 | 7/2002 | Tearney et al. | |
| 6,445,939 B1 | 9/2002 | Swanson et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,706,004 B2 | 3/2004 | Tearney et al. | |
| 6,879,851 B2 | 4/2005 | McNamara et al. | |
| 6,891,984 B2 | 5/2005 | Petersen et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,414,779 B2 | 8/2008 | Huber et al. | |
| 7,415,049 B2 | 8/2008 | Flanders et al. | |
| 7,625,366 B2 | 12/2009 | Atlas | |
| 7,713,281 B2 | 5/2010 | Leeflang et al. | |
| 7,736,301 B1 | 6/2010 | Webler et al. | |
| 7,801,343 B2 | 9/2010 | Unal et al. | |
| 7,813,609 B2 | 10/2010 | Petersen et al. | |
| 7,848,791 B2 | 12/2010 | Schmitt et al. | |
| 7,875,049 B2 | 1/2011 | Eversull et al. | |
| 7,916,387 B2 | 3/2011 | Schmitt | |
| 7,935,060 B2 | 5/2011 | Schmitt et al. | |
| 8,116,605 B2 | 2/2012 | Petersen et al. | |
| 8,206,377 B2 | 6/2012 | Petroff | |
| 8,252,015 B2 | 8/2012 | Leeflang et al. | |
| 8,325,419 B2 | 12/2012 | Schmitt | |
| 8,358,461 B2 | 1/2013 | Huber et al. | |
| 8,412,312 B2 | 4/2013 | Judell et al. | |
| 8,449,468 B2 | 5/2013 | Petersen et al. | |
| 8,478,384 B2 | 7/2013 | Schmitt et al. | |
| 8,478,387 B2 | 7/2013 | Xu | |
| 8,503,844 B2 | 8/2013 | Petersen et al. | |
| 8,581,643 B1 | 11/2013 | Schmitt | |
| 8,582,109 B1 | 11/2013 | Schmitt | |
| 8,582,619 B2 | 11/2013 | Adler | |
| 8,582,934 B2 | 11/2013 | Adler et al. | |
| 8,676,299 B2 | 3/2014 | Schmitt et al. | |
| 8,687,201 B2 | 4/2014 | Adler | |
| 8,753,281 B2 | 6/2014 | Schmitt et al. | |
| 8,786,336 B1 | 7/2014 | Schmitt | |
| 8,831,321 B1 | 9/2014 | Elbasiony | |
| 8,834,036 B2 | 9/2014 | Aihara | |
| 8,857,220 B2 | 10/2014 | Bhagavatula et al. | |
| 8,861,900 B2 | 10/2014 | Bhagavatula et al. | |
| 8,902,941 B2 | 12/2014 | Schmitt | |
| 8,926,590 B2 | 1/2015 | Petroff | |
| 8,942,524 B2 | 1/2015 | Hung | |
| 8,948,228 B2 | 2/2015 | Adler | |
| 8,948,613 B2 | 2/2015 | Schmitt et al. | |
| 8,953,911 B1 | 2/2015 | Xu et al. | |
| 9,007,696 B2 | 4/2015 | Petersen et al. | |
| 9,069,396 B2 | 6/2015 | Adler et al. | |
| 9,091,524 B2 | 7/2015 | Adler et al. | |
| 9,138,147 B2 | 9/2015 | Schmitt et al. | |
| 9,164,240 B2 | 10/2015 | Schmitt et al. | |
| 9,173,591 B2 | 11/2015 | Elbasiony et al. | |
| 9,351,698 B2* | 5/2016 | Dascal | A61B 6/463 |
| 9,404,731 B2 | 8/2016 | Adler et al. | |
| 9,417,052 B2 | 8/2016 | Adler | |
| 9,435,956 B1 | 9/2016 | Xu et al. | |
| 9,462,950 B2 | 10/2016 | Xu | |
| 9,488,464 B1 | 11/2016 | Schmitt | |
| 9,526,424 B2 | 12/2016 | Judell et al. | |
| 9,572,495 B2 | 2/2017 | Schmitt et al. | |
| 9,610,064 B2 | 4/2017 | Adler et al. | |
| 9,622,706 B2 | 4/2017 | Dick et al. | |
| 9,702,687 B2 | 7/2017 | Schmitt | |
| 9,702,762 B2 | 7/2017 | Friedman et al. | |
| 9,833,221 B2 | 12/2017 | Hutchins et al. | |
| 9,864,140 B2 | 1/2018 | Adler et al. | |
| 9,907,527 B2 | 3/2018 | Dascal et al. | |
| 9,940,723 B2 | 4/2018 | Gopinath et al. | |
| 9,983,356 B2 | 5/2018 | Schmitt et al. | |
| 9,989,945 B2 | 6/2018 | Adler et al. | |
| 9,996,921 B2 | 6/2018 | Ambwani et al. | |
| 10,006,753 B2 | 6/2018 | Schmitt et al. | |
| 10,028,725 B2 | 7/2018 | Petroff | |
| 10,089,755 B2 | 10/2018 | Griffin et al. | |
| 10,109,058 B2 | 10/2018 | Ambwani et al. | |
| 10,140,712 B2 | 11/2018 | Ambwani | |
| 10,172,582 B2 | 1/2019 | Dascal et al. | |
| 10,222,956 B2 | 3/2019 | Gopinath et al. | |
| 10,327,726 B2 | 6/2019 | Dascal et al. | |
| 10,331,099 B2 | 6/2019 | Adler et al. | |
| 10,335,039 B2 | 7/2019 | Xu | |
| 10,338,795 B2 | 7/2019 | Gopinath et al. | |
| 10,342,502 B2 | 7/2019 | Dascal et al. | |
| 10,453,190 B2 | 10/2019 | Griffin | |
| 10,453,196 B2 | 10/2019 | Ambwani | |
| 10,499,813 B2 | 12/2019 | Adler | |
| 11,241,154 B2* | 2/2022 | Adler | A61B 5/0066 |
| 2002/0161351 A1 | 10/2002 | Samson et al. | |
| 2003/0051728 A1* | 3/2003 | Lloyd | A61M 11/001 128/200.14 |
| 2003/0077036 A1 | 4/2003 | Tanaka et al. | |
| 2003/0175000 A1* | 9/2003 | Caracci | G02B 6/32 385/33 |
| 2003/0236453 A1* | 12/2003 | Furnish | A61B 5/0084 600/341 |
| 2005/0148866 A1 | 7/2005 | Gunderson | |
| 2005/0149104 A1* | 7/2005 | Leeflang | A61B 17/3439 606/198 |
| 2005/0149105 A1 | 7/2005 | Leeflang et al. | |
| 2005/0201662 A1 | 9/2005 | Petersen et al. | |
| 2006/0095065 A1 | 5/2006 | Tanimura et al. | |
| 2006/0217755 A1 | 9/2006 | Eversull et al. | |
| 2009/0005706 A1 | 1/2009 | Miyata et al. | |
| 2009/0018393 A1 | 1/2009 | Dick et al. | |
| 2009/0174931 A1 | 7/2009 | Huber et al. | |
| 2009/0262361 A1 | 10/2009 | Tanioka et al. | |
| 2009/0306520 A1 | 12/2009 | Schmitt et al. | |
| 2010/0076320 A1 | 3/2010 | Petersen et al. | |
| 2010/0160952 A1 | 6/2010 | Leeflang et al. | |
| 2011/0137124 A1 | 6/2011 | Milner et al. | |
| 2011/0157686 A1 | 6/2011 | Huber et al. | |
| 2011/0178413 A1 | 7/2011 | Schmitt et al. | |
| 2011/0190586 A1 | 8/2011 | Kemp | |
| 2012/0075638 A1 | 3/2012 | Rollins et al. | |
| 2012/0310081 A1* | 12/2012 | Adler | A61B 5/6852 600/427 |
| 2013/0039621 A1 | 2/2013 | Aihara | |
| 2013/0051728 A1* | 2/2013 | Petroff | A61B 5/0084 65/399 |
| 2013/0219969 A1 | 8/2013 | Bhagavatula et al. | |
| 2013/0223787 A1 | 8/2013 | Bhagavatula et al. | |
| 2013/0310698 A1 | 11/2013 | Judell et al. | |
| 2014/0024931 A1 | 1/2014 | Winston et al. | |
| 2014/0094697 A1* | 4/2014 | Petroff | A61B 5/0066 600/427 |
| 2014/0114182 A1 | 4/2014 | Petersen et al. | |

(56) References Cited

U.S. PATENT DOCUMENTS

| | | |
|---|---|---|
| 2014/0142427 A1 | 5/2014 | Petroff |
| 2014/0142432 A1 | 5/2014 | Hutchins et al. |
| 2014/0142436 A1 | 5/2014 | Hutchins et al. |
| 2014/0178002 A1 | 6/2014 | Hung |
| 2014/0180067 A1 | 6/2014 | Stigall et al. |
| 2014/0180071 A1 | 6/2014 | Stigall et al. |
| 2014/0187929 A1 | 7/2014 | Schmitt et al. |
| 2014/0270436 A1* | 9/2014 | Dascal ............ A61B 5/0073 382/130 |
| 2014/0276011 A1 | 9/2014 | Schmitt et al. |
| 2014/0309526 A1 | 10/2014 | Balbas et al. |
| 2014/0379269 A1 | 12/2014 | Schmitt |
| 2015/0119707 A1 | 4/2015 | Schmitt |
| 2015/0186193 A1 | 7/2015 | Jain et al. |
| 2015/0297373 A1 | 10/2015 | Schmitt et al. |
| 2015/0370229 A1 | 12/2015 | Adler et al. |
| 2016/0022208 A1 | 1/2016 | Gopinath |
| 2016/0058307 A1 | 3/2016 | Svanerudh |
| 2016/0070066 A1 | 3/2016 | Schmitt et al. |
| 2017/0143296 A1 | 5/2017 | Peterson et al. |
| 2017/0188831 A1* | 7/2017 | Adler ............ A61B 6/504 |
| 2017/0188912 A1 | 7/2017 | Halac et al. |
| 2017/0261378 A1 | 9/2017 | Friedman et al. |
| 2017/0301084 A1 | 10/2017 | Gopinath |
| 2017/0325712 A1 | 11/2017 | Gopinath |
| 2018/0003482 A1 | 1/2018 | Schmitt |
| 2018/0177404 A1 | 6/2018 | Liu |
| 2018/0192957 A1 | 7/2018 | Schmitt et al. |
| 2018/0192983 A1 | 7/2018 | Dascal et al. |
| 2018/0225830 A1 | 8/2018 | Gopinath et al. |
| 2018/0293730 A1 | 10/2018 | Ambwani et al. |
| 2018/0296111 A1 | 10/2018 | Deno et al. |
| 2018/0306569 A1 | 10/2018 | Schmitt et al. |
| 2019/0035114 A1 | 1/2019 | Griffin et al. |
| 2019/0099237 A1 | 4/2019 | Booker et al. |
| 2019/0220980 A1 | 7/2019 | Ambwani et al. |
| 2019/0307412 A1 | 10/2019 | Dascal et al. |
| 2019/0343409 A1 | 11/2019 | Schmitt et al. |
| 2019/0380594 A1 | 12/2019 | Schmitt et al. |

FOREIGN PATENT DOCUMENTS

| | | |
|---|---|---|
| JP | 2012-110632 A | 6/2012 |
| JP | 2012-531972 A | 12/2012 |
| JP | 2013-056154 A | 3/2013 |
| JP | 2014525761 A | 10/2014 |
| JP | 2015-534896 A | 12/2015 |
| JP | 2016-506273 A | 3/2016 |
| JP | 2016-506276 A | 3/2016 |
| JP | 2016-512616 A | 4/2016 |
| JP | 2016-093350 A | 5/2016 |
| JP | 2016-104151 A | 6/2016 |
| JP | 2016-516466 A | 6/2016 |
| WO | 2014142789 A1 | 9/2014 |
| WO | 2014/175853 A1 | 10/2014 |

OTHER PUBLICATIONS

Japanese Office Action issued in Appln. No. 2020-539684 issued Feb. 17, 2023.
International Search for PCT/US2018/053960 mailed Jan. 11, 2019. 2 pgs.
Office Action issued in EP Appln. No. 22185311.2 mailed Sep. 4, 2023 (4 pages).
Search Report by Registered Search Organization for Application No. JP 2020-539684 dated Aug. 31, 2022, pp. 1-9.
European Office Action for EP Application No. 22185311.2 dated Nov. 26, 2024, 6 pages.
Japanese Office Action from JP Appl. No. 2020-539684, dated Jan. 24, 2025, pp. 1-12.
Japanese Office Action from JP Appl. No. 2023-213262, dated Jan. 28, 2025, pp. 1-6.

* cited by examiner

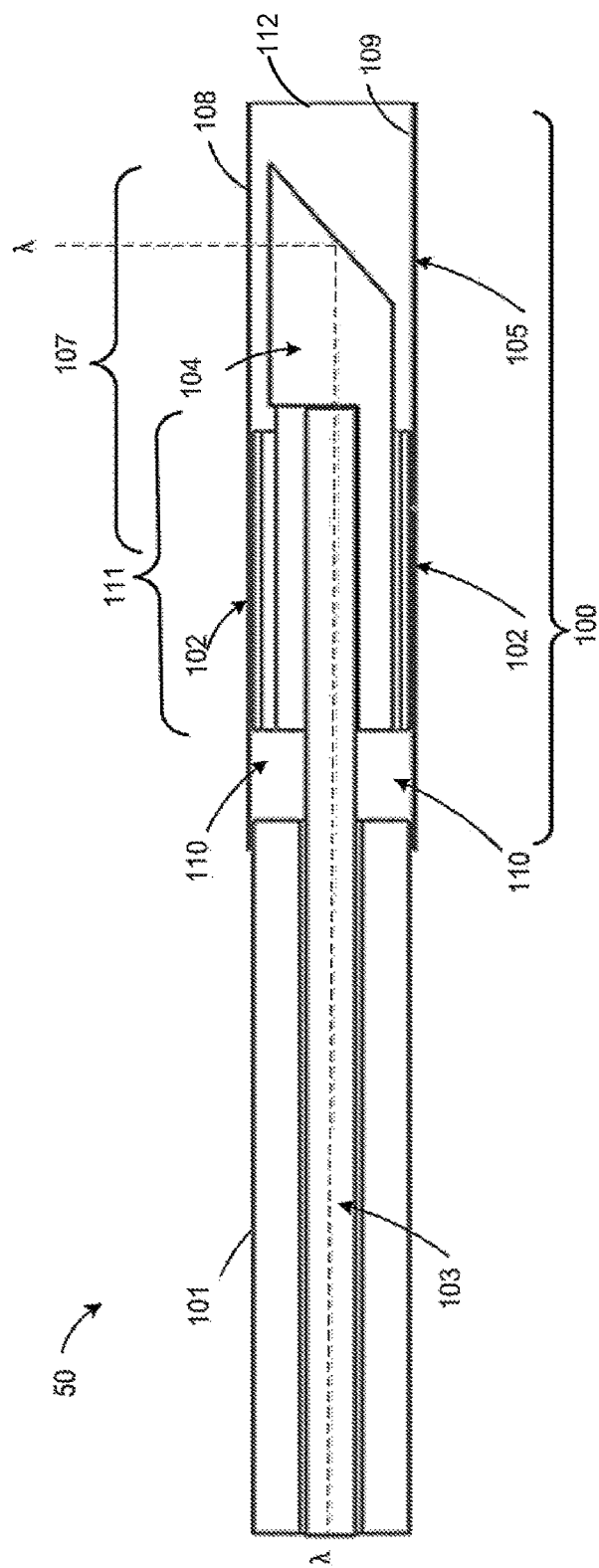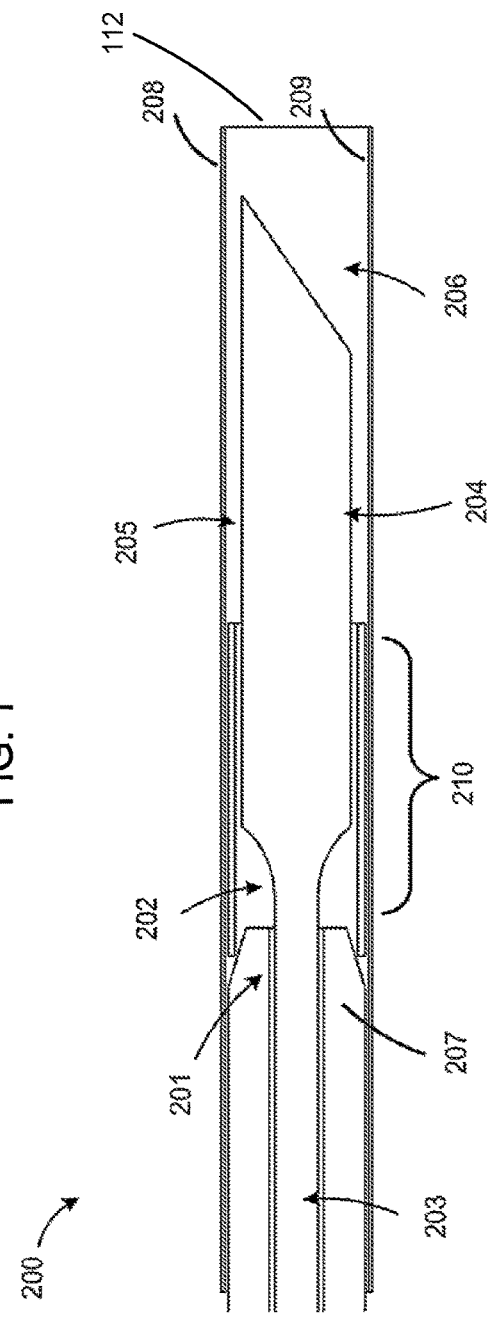

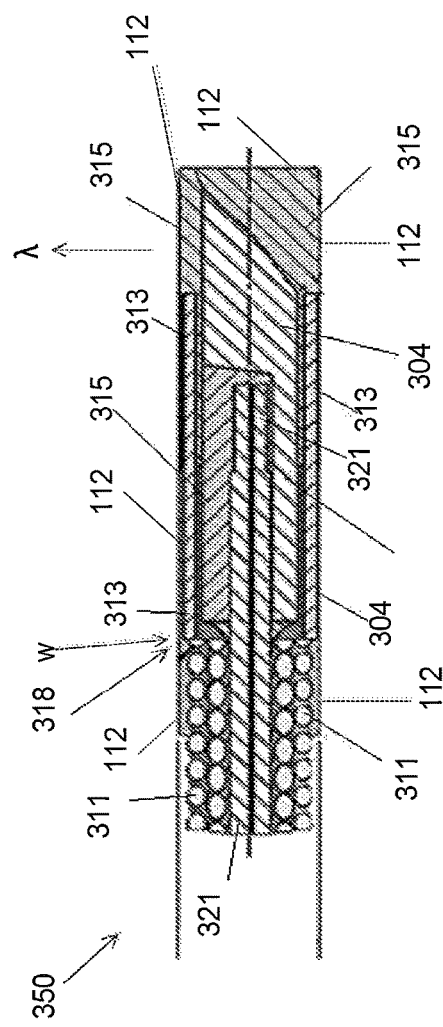
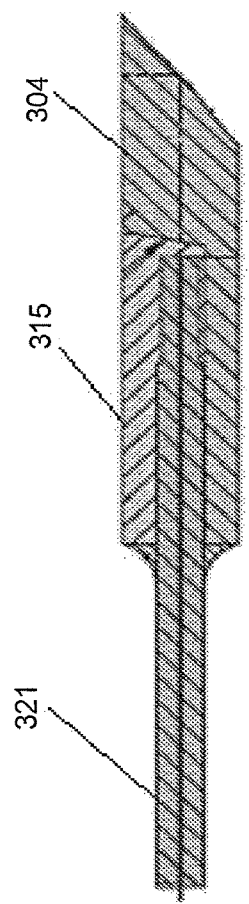
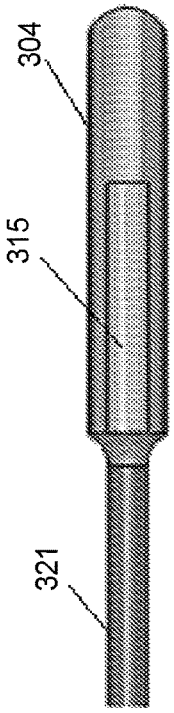
FIG. 3C
FIG. 3D
FIG. 3E

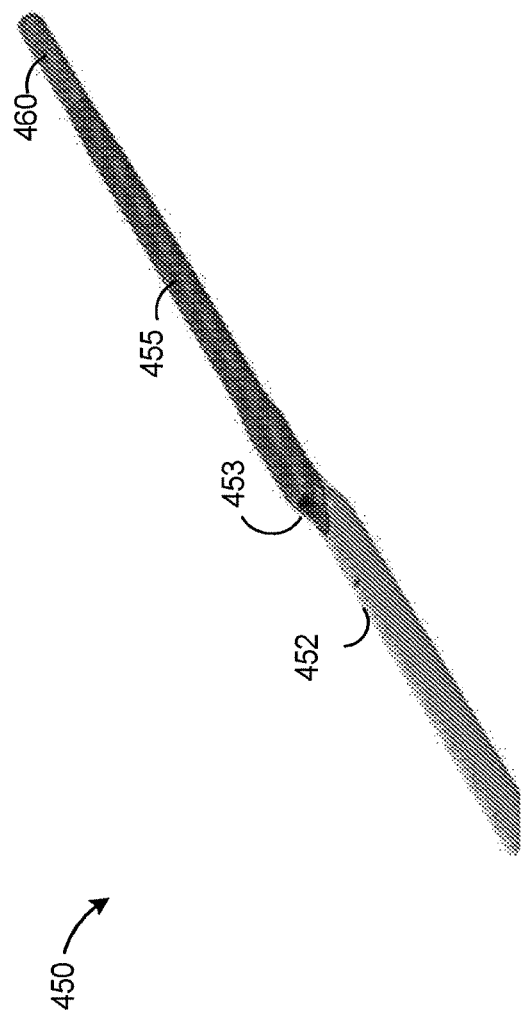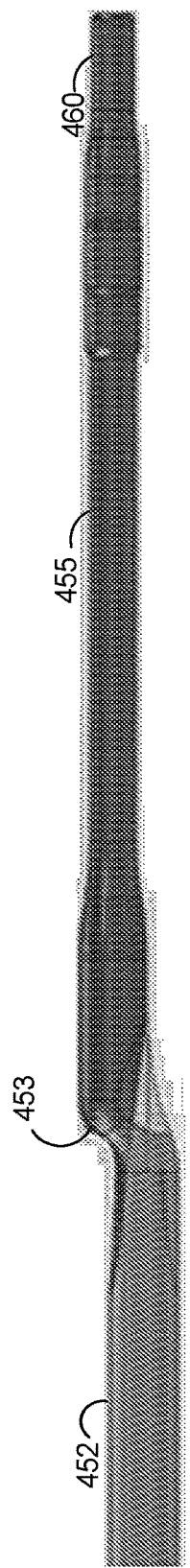
FIG. 7A
FIG. 7B
FIG. 7C

INTRAVASCULAR DATA COLLECTION PROBES AND RELATED ASSEMBLIES

RELATED APPLICATIONS

The present application is a continuation of U.S. application Ser. No. 17/750,978, filed on May 23, 2022, which is a continuation of U.S. application Ser. No. 16/149,886, filed on Oct. 2, 2018, which claims priority to and the benefit of U.S. Provisional Patent Application No. 62/567,189, filed on Oct. 2, 2017, the disclosures all of which are herein incorporated by reference in their entirety.

BACKGROUND

Various types of intravascular probes have been developed to image lumens. Some of these probes use an optical fiber as a rotatable element to send and receive optical signals. Other rotating transceivers are used for other probe designs. Spinning an optical fiber and an optical beam director as part an intravascular probe can result in rotational variations, imbalances, and twisting of the fiber. These and other unwanted effects that plague such rotatable probes can be generally described as non-uniform rotational distortion or "NURD."

For example, the geometrical accuracy along the lateral direction may be affected by NURD), resulting in a stretched or compressed appearance of the lateral dimension of object being imaged. This can result in improper detections such as when imaging a strut in an artery, for example. The geometrical accuracy along the pullback direction may also be affected by non-uniform relative pullback speed between the imaging element and the tissue being imaged. These and other types of noise can contribute to imaging artifacts such as chatter and others.

It is desirable to reduce or prevent NURD when designing probes and systems that use them for data collection in a lumen or other environment in order to reduce imaging artifacts and other negative design consequences that follow from NURD. For example, U.S. Pat. No. 6,891,984 entitled "Scanning miniature optical probes with optical distortion correction and rotational control" describes the use of viscous damping fluid to reduce or prevent NURD effects in the context of imaging probes. The use of such fluids is suitable for use in some embodiments, but other approaches to resolve NURD more broadly remain outstanding.

Accordingly, a need exists for systems, designs and methods to reduce or prevent NURD such that its negative effects on data collected using rotating probes and/or components thereof can be mitigated or removed.

The present disclosure addresses this need and others.

SUMMARY

In part, the disclosure relates to probe embodiments that reduce length of a section of probe that has greater stiffness compared to torque wire or other sections of probe. This reduction in stiff section length can be implemented such as with regard to an imaging assembly that includes a lens, marker band, and an optical fiber section. A reduction in stiffness length has been evaluated and found to reduce NURD in various probe configurations. A reduction in NURD also can result in a reduction in other unwanted effects such as chatter.

In part, the disclosure relates to intravascular data collection probe. The probe may include a marker band defining a bore, an outer surface, a first end and a second end, the marker band having a band length, the marker band comprising a radiopaque material; a lens defining a beam directing surface, the lens partially disposed in the bore, wherein the beam directing surface extends past the second end; an optical fiber disposed in the marker band, wherein a section of the optical fiber extends from the first end of the marker band, the optical fiber optically coupled to the lens.

The probe may further include a jacket defining a jacket bore, wherein the marker band, the lens, and a section of the optical fiber are disposed in the jacket bore. The probe may further include a torque wire defining a torque wire bore and a torque wire end face, wherein the optical fiber extending from the marker band is disposed in the torque wire bore, wherein the first end of the marker band is joined to the torque wire end face. In one embodiment, the marker band is joined to the torque wire end face by a butt weld. The probe may further include a jacket defining a jacket bore, wherein the marker band, the lens, and a section of the optical fiber are disposed in the jacket bore. In one embodiment, the first end of the marker band and the torque wire end face are disposed in the jacket bore.

In one embodiment, the torque wire end face defines a bevel oriented at a bevel angle relative to a longitudinal axis of the torque wire bore, wherein the end face is welded to the first end of the marker band. In one embodiment, lens is a molded unitary lens defining an elongate optical fiber receiving section having a fiber section length and a beam directing surface. In one embodiment, a first section of the optical fiber is disposed in the optical fiber receiving section, wherein a portion of the first section of the optical fiber is disposed within the marker band bore. In one embodiment, the torque wire defines a first outer diameter at the first endface and a second outer diameter at the second endface, wherein the second outer diameter is less than the first outer diameter. In one embodiment, the second outer diameter spans a distance from the second end face until the second outer diameter reaches a step up to the first outer diameter.

In one embodiment, a portion of the second end of the torque wire that defines the second diameter is disposed within the bore of the marker band. In one embodiment, the bevel angle ranges from about 20 degrees to about 60 degrees. In one embodiment, torque wire has a first stiffness, wherein marker band has a second stiffness greater than the first stiffness, wherein sum of length of marker band and length of lens extending from marker band defines a stiffness section. In one embodiment, the length of the stiffness section ranges from about 2 mm to about 3 mm. In one embodiment, the probe is configured to reduce chatter when rotating the probe and collecting image data.

The probe may further include a coating. The coating is disposed on or relative to the lens such that the lens and the coating define a compound lens system. In one embodiment, the marker band is substantially cylindrical. In one embodiment, the torque wire is connected to the marker band by a joint substantially in a single plane. In one embodiment, the lens is a molded unitary lens defining an elongate optical fiber receiving section having a fiber section length and a beam directing surface. In one embodiment, the marker band and torque wire are joined by a flexible junction. In one embodiment, the fiber section length and the band length overlap.

In one embodiment, an elongate cylindrical component of a probe includes an end, wherein a bevel is defined by or otherwise formed from the end of the component. The bevel has an associated angle relative to an axis of the cylindrical component that ranges from about 20 degrees to about 60 degrees. In one embodiment, the elongate component is a torque wire. In one embodiment, the component is a ring or band such as a marker band that includes a radiopaque material. In one embodiment, the probes disclosed herein include a joint or hinge that couples, connects, or otherwise spans two adjacent elongate components of the probe. The joint or hinge is flexible such that it self-aligns when the probe or a portion thereof rotates.

In one embodiment, a probe that includes a torque wire, a marker band that includes a radiopaque material and an optical fiber disposed in the core of the torque wire and a section of the optical fiber is disposed within the marker band. In one embodiment, the probe has a section that is stiff relative to one or more sections of the torque wire. This stiff section has a section length in one embodiment. In one embodiment, reducing the section length reduces NURD. In one embodiment, the length of the stiff section is less than or equal to about 3.5 mm. The In one embodiment, the length of the stiff section is less than or equal to about 3.4 mm. In one embodiment, the length of the stiff section is less than or equal to about 3.3 mm. In one embodiment, the length of the stiff section is less than or equal to about 3.2 mm. In one embodiment, the length of the stiff section is less than or equal to about 3.1 mm. In one embodiment, the length of the stiff section is less than or equal to about 3.0 mm. In one embodiment, the length of the stiff section is less than or equal to about 2.9 mm. In one embodiment, the length of the stiff section is less than or equal to about 2.8 mm. In one embodiment, the length of the stiff section is less than or equal to about 2.7 mm. In one embodiment, the length of the stiff section is less than or equal to about 2.6 mm. In one embodiment, the length of the stiff section is less than or equal to about 2.5 mm. In one embodiment, the length of the stiff section is less than or equal to about 2.4 mm. In one embodiment, the length of the stiff section is less than or equal to about 2.3 mm. In one embodiment, the length of the stiff section is less than or equal to about 2.2 mm. In one embodiment, the length of the stiff section is less than or equal to about 2.1 mm. In one embodiment, the length of the stiff section is less than or equal to about 2.0 mm. In one embodiment, the length of the stiff section is less than or equal to about 1.9 mm. In one embodiment, the length of the stiff section is less than or equal to about 1.8 mm. In one embodiment, the length of the stiff section is greater than about 2.0 mm and less than about 3.2 mm. In one embodiment, the length of the stiff section is greater than about 2.0 mm and less than about 2.5 mm.

In one embodiment, the probe includes a lens such as molded lens. The molded lens can include a trough or channel. An elongate substantially cylindrical section of the molded lens is disposed within the marker band. In one embodiment, the length of the section of the molded lens disposed in the marker band is less than about 2.4 mm. In one embodiment, the length of the section of the molded lens disposed in the marker band ranges from about 0.8 mm to about 1.6 mm. In one embodiment, the distance from an end face of the marker band abutting or adjacent to the torque wire to the distal end of the lens ranges from about 2 mm to about 2.8 mm. In one embodiment, the distance from an end face of the marker band abutting or adjacent to the torque wire to the distal end of the lens ranges from about 2 mm to about 3 mm.

In one embodiment, dipping or adhesives can be used to form a tube or shell or other layer around the imaging assembly having an OD less than or equal to the OD of the torque wire. In one embodiment, various end points can be selected as the basis for stiffness measures. In one embodiment, the stiffness measurements are made from the tip of the lens to where coil of torque wire bends based on size of the weld and number of coils of torque wire welded.

In one embodiment, the marker band may be glued, welded, and/or soldered to torque wire. The torque wire may have bevel or L-Grind. When glued, the marker band may be spaced away from the torque wire. In one embodiment, the outer tubing may be left in place or removed after gluing or otherwise fixing or attaching the components of the imaging assembly and/or probe. In one embodiment, conformal coatings can be applied to the imaging assembly. Multi-layer extruded materials can be used. In one embodiment, a jacket is used to mold or shape a material and then the jacket is split and peel away to leave a material layer around a portion or all of the imaging assembly. In some embodiments, the jacket is left in place. In one embodiment, the jacket is disposed such that it straddles or otherwise covers a weld such as a butt weld or butt joint used to attach the torque wire and the marker band. The jacket can include PET in one embodiment. The jacket has a jacket bore that can receive one or more elements of imaging assembly such as lens, marker band, and section of optical fiber in optical communication with lens.

Although, the disclosure relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation.

Other features and advantages of the disclosed embodiments will be apparent from the following description and accompanying drawings.

BRIEF DESCRIPTION OF DRAWINGS

The figures depicted and described herein are not necessarily to scale, emphasis instead generally being placed upon illustrative principles. The figures are to be considered illustrative in all aspects and are not intended to limit the disclosure, the scope of which is defined only by the claims.

FIG. 1 is a schematic diagram that illustrates a cross-section view of a probe that includes an optical fiber, a torque wire, a lens and other components according to an illustrative embodiment of the disclosure.

FIG. 2 is a schematic diagram that illustrates an imaging core assembly with a torque wire that includes a beveled end according to an illustrative embodiment of the disclosure.

FIG. 3C is a cross-sectional view that illustrates an imaging core assembly that includes a torque wire with a butt weld joint according to an illustrative embodiment of the disclosure.

FIG. 3D is a cross-sectional view of a data collection probe in which a molded lens is shown attached to an optical fiber according to an illustrative embodiment of the disclosure.

FIG. 3E is a top view of the data collection probe of FIG. 3D in which a molded lens is shown attached to an optical fiber according to an illustrative embodiment of the disclosure.

FIGS. 7A-7C are schematic diagrams that illustrate the arrangement of a catheter and some of its components and subassemblies suitable for use with a probe having an imaging assembly.

DETAILED DESCRIPTION

Figure 3A:
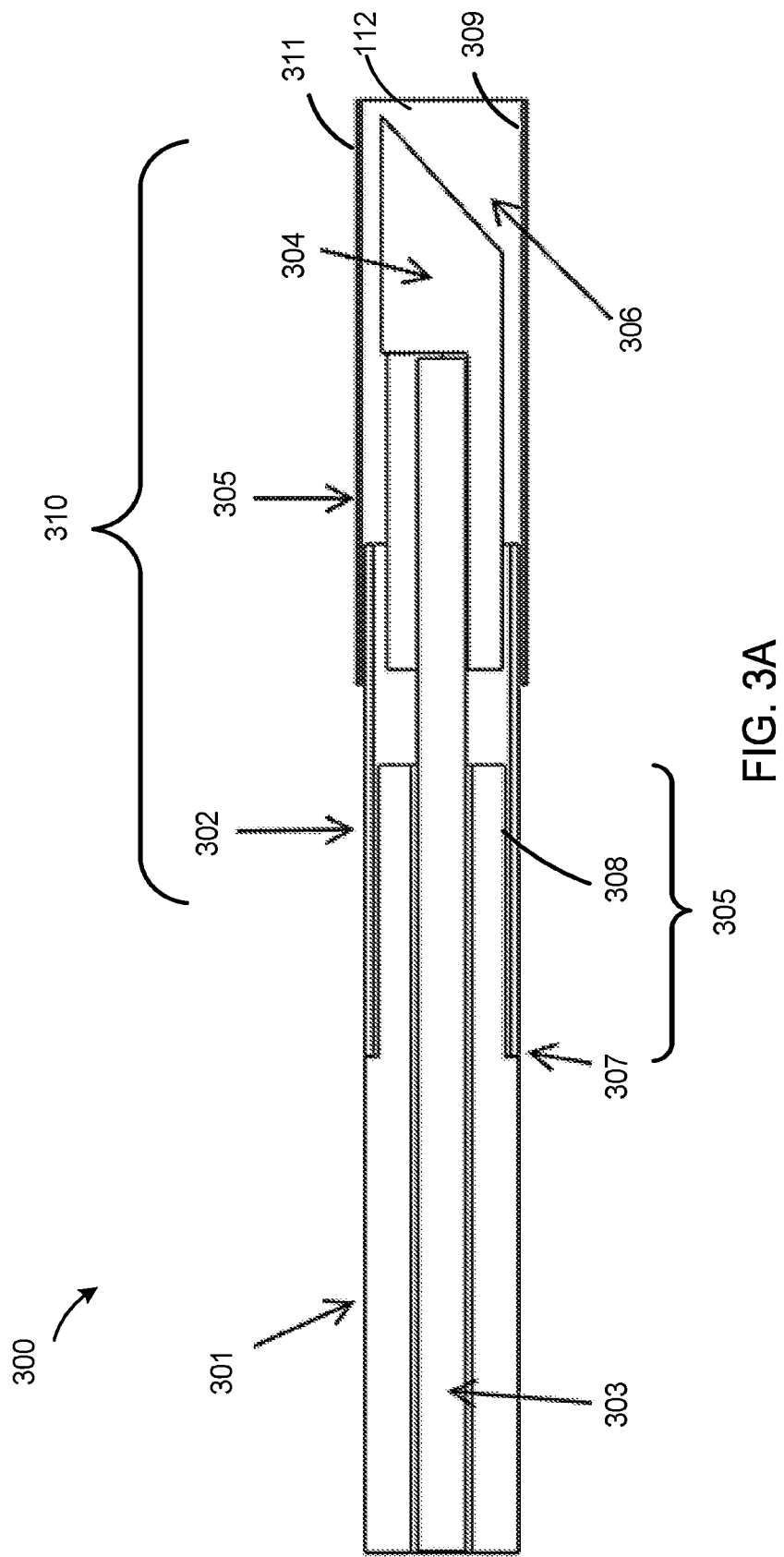
FIG. 3A is a schematic diagram that illustrates an imaging core assembly that includes a torque wire with L-grind detail according to an illustrative embodiment of the disclosure.

In part, the disclosure relates to probes that reduce NURD and improve imaging. In one embodiment, a probe is described that constrains the outer diameter of the probe to match the outer diameter of the torque wire used to rotate the probe and the optical assembly located distal to the rotating drive source. A stiff section that overlaps with one or more sections of the lens is designed to be reduced to a minimum value or within a range of allowed values. Exemplary stiff section values are described in more detail herein. The stiff section can be commensurate with the marker band. In one embodiment, the probe is designed to increase concentricity to a relative maximum or maximum value and reduce angularity to a relative minimum or minimum value. The stiff section is a relative stiffness compared to other sections of the probe or the imaging assembly in various embodiments.

In one embodiment, the probe includes a lens such as molded lens. The lens may be coated to create a compound lens system. An elongate substantially cylindrical section of the molded lens is disposed within the marker band. In one embodiment, the length of the section of the molded lens disposed in the marker band is the stiffness section length. In one embodiment, the length of the section of the molded lens disposed in the marker band is less than about 2.4 mm. In one embodiment, the length of the section of the molded lens disposed in the marker band ranges from about 0.8 mm to about 1.6 mm. In one embodiment, a subset of the torque wire is ground to be received by the marker band.

Various embodiments described herein use a torque wire that is paired with other optical and mechanical elements such that the torque wire can rotate within a catheter having an imaging window with minimal or reduced NURD caused by the flexing of the wire during rotation. The current state of the art uses a dual layer torque coil. Other torque wires can be used. The torque wire is typically attached to an imaging core assembly (also referred to as an imaging assembly) when used as part of an imaging probe. The imaging probe can be used in an intravascular capacity and has adjustments specified in terms of section stiffness to reduce NURD and improve navigation in tortuous vessels.

In some embodiments, the imaging core assembly includes one or marker bands welded to the outer diameter of the torque wire. In some embodiments, the imaging core assembly includes two marker bands welded to the outer diameter of the torque wire. Such an implementation has an increased outer diameter at the location of the marker bands, which may increase non-uniform rotational distortion (NURD). Additionally, any non-concentricity of the marker bands or the lens assembly may also increase NURD. Various probes designs also include a relatively long stiff section, which also has potentially negative impact on NURD. These designs and others can also result in the lens of the imaging assembly being oriented a slight angle relative to the catheter which receives the imaging probe. This may increase NURD.

Various approaches have been analyzed such that new designs with various NURD mitigating features can be implemented. For example, some of the embodiments discussed in more detail below relate to probes that avoid marker bands on the outer diameter of the torque wire an imaging probe, allowing for a reduction in NURD. This can, in turn, result in improved imaging when detecting stent struts.

To mitigate NURD, the present disclosure relates, in part, probes without marker bands on the outer diameter of the torque wire. This can be accomplished with various arrangements, welds, joins, joints, linkages, and lens choices and orientation and overlap of the foregoing as described in more detail herein. In addition, it is been determined that be reducing the length of one or more stiff sections of the probe and/or imaging assembly, NURD is reduced. Overlapping probe components is used to reduce stiff section lengths in some embodiments. Thus, a portion of a lens can overlap with a marker band in some embodiments. A jacket or sleeve and adhesive disposed in the sleeve can also be arranged to overlap with a section of the optical fiber, the molded lens, and a portion of the marker band. Typically, the optical fiber is disposed in a bore or channel of molded lens attached to molded lens with adhesive. Adhesive is also used to secure the marker band relative to the molded lens and sleeve/sheath/jacket. In general, selecting geometries and arrangements for probe components that increase concentricity and that reduce angularity are also advantageous.

In part, the disclosure relates to rotatable components of data collection probes and rotatable probes that are designed to reduce NURD or otherwise be centrally rotationally balanced. The geometrical accuracy along the lateral direction may be affected by NURD, resulting in a stretched or compressed appearance of the lateral dimension of the struts. As a result, probe designs that reduce imaging artifacts may also improve the detection of stent struts. As a result, the disclosure also relates to methods of reducing, mitigating or otherwise managing NURD to improve imaging or other data collection using a rotatable probe.

The following discussion presents detailed descriptions of the several embodiments of an imaging probe that avoids marker bands on the outer diameter of the imaging core assembly. In this way, by not increasing the diameter of the probe over a segment of its length through the use of an elongate radiopaque band defining a bore, NURD can be further reduced. It also becomes easier to move and position the imaging assembly through a torturous environment in some embodiments. The embodiments of the present disclosure have wide application, and may be used on any probes, pressure sensors, torque wire-based devices and components thereof.

Some embodiments of probes are suitable for use as disposable intravascular data collection probes such as OCT, IVUS, or combination imaging probes. Further, although generally described in the context of data collection, medical procedures and medical devices, in part, the devices and methods described herein also generally relate to probes for lumens and thus have applications outside of the medical field as such devices can be adapted or configured, whole or in part. Accordingly, the following descriptions and illustrations herein should be considered illustrative in nature, and not limiting the scope of the invention, as claimed.

In part, the disclosure includes features that relate to an imaging core assembly. FIG. 1 illustrates one embodiment of an exemplary data collection probe 50 that includes an imaging core assembly 100 that includes no marker bands 102 on the outer diameter of the probe. In one embodiment, the imaging core assembly attaches to a torque wire such as torque wire 101. The imaging core assembly can include a sleeve, sheath, or jacket 112 (generally referred to as a jacket) that can have a tube or cylindrical geometry. The jacket 112 can be filled or contacted with adhesive that secures the molded lens and fiber to the marker band and the jacket. In one embodiment, the sleeve or jacket 112 extends over the marker band and a joint or weld attaching the torque wire to the marker band. In various embodiments, the sleeve or jacket 112 defines a bore in which the lens, marker band, a segment of the optical fiber, and a section of the torque wire are disposed.

Adhesive disposed in the jacket 112 can also attach other components disposed with the sleeve. In various embodiments, probe designs avoid increasing outer diameter beyond outer diameter of torque wire. The imaging core assembly 100 includes a portion of torque wire 101 and a marker band 102. In some embodiments, the imaging core 100 does not include the torque wire 101 but is coupled or other connected thereto.

In some embodiments, the end of the torque wire 101 may be beveled at an angle. The angle can be used to facilitate a joint, a weld and/or the wicking of weld or adhesive material. In other embodiments, the end of the torque wire 101 may be modified by an L-grind. The bevel or the L-grind at the end of the torque wire 101 is intended to help center the marker band 102 in order to keep the entire imaging core assembly 100 concentric. It can also increase joint/weld strength. In some embodiments, the torque wire 101 may be smooth. In FIG. 1, light or electromagnetic radiation λ is shown propagating along a longitudinal axis of the optical fiber 103 and then being directed out into a lumen or other environment by lens 104. Reference to λ in figures shows light entering or exiting probe.

In one embodiment, the marker band 102 is positioned on the inner diameter of the imaging core assembly 100. In other embodiments, the marker band 102 may be flush against the outer diameter 108 in order to minimize the outer diameter 108 of the imaging core assembly 100. In one embodiment, the inner diameter 109 and outer diameter 108 of the imaging assembly corresponds to that of the sleeve or jacket 112 that surrounds a portion of the lens and marker band. In some embodiments, the marker band 102 may be of an equal or smaller outer diameter than the torque wire 101. The marker band 102 is positioned along the inner diameter 109 of the imaging core assembly 100 in order to minimize NURD. Lens 104 has a fiber receiving section 111 that receives optical fiber 103. In general, reducing length of section 100 and subsections thereof is desirable in various embodiments.

In one embodiment, the marker band 102 may be adhered to the torque wire 101. In one embodiment, the marker band 102 may be spaced away from the torque wire 101 by a gap 110. In other embodiments, the marker band 102 may touch the torque wire 101 such as being welded thereto. In this embodiment, the outer diameter 108 of the imaging core assembly 100 is reduced compared embodiment with markers on top of torque wire resulting in reduced NURD. The stiff section 107 of the imaging core assembly 100—that includes the marker band 102 and molded lens 104—is moved away from the end of the torque wire 101. The overlap of band 102 and lens 104 reduces overall length of stiff section.

In some embodiments, the torque wire 101 and the marker band 102 may be adhered using a glue material. In other embodiments, the torque wire 101 and the marker band 102 may be adhered using any suitable material such as, but not limited to welds, adhesives, compression fit, shrink fit materials, PET, nylon, and others. In one embodiment, the material that attaches or adheres the marker band 102 and torque wire 101 together serves as a flexible junction between the torque wire 101 and the marker band 102, thus the stiff section 107 is minimized and subsequently the NURD is minimized.

In other embodiments, the marker band 102 may be welded or soldered to the torque wire 101. In one embodiment, the marker band 102 may be welded to the torque wire 101. The torque wire 101 may include a bevel or L-grind. As shown, in FIG. 3 the L-grind can be viewed as a shell or object formed by rotating an L around an axis parallel to the vertical longer edge of the "L." An L grind has a step such that the outer diameter of the torque wire steps in and drops to a lower outer diameter. The length of the section having the smaller outer diameter corresponds to the length of the vertical portion of the "L" with the horizontal portion of the "L" corresponding to the step in distance from the longer unground outer diameter of the "L."

In one embodiment, the location of the weld is selected as a means of aligning the torque wire 101 relative to other probe components. In one embodiment, a hinge or joint is used to connect one or more components arranged along the cylindrical axis of the optical fiber and torque wire as shown such that when the torque wire rotates the hinge or joint flexes such that the elements in the probe are aligned and/or rotationally balanced. This can occur as the hinge or join spins up and reaches a stable rotational state that pulls other components of the probe into a balanced rotational configuration.

At the center of the imaging core assembly 100 is a molded lens 104, which is bonded to an optic fiber 103. The bonded optic fiber 103 and molded lens 104 is slid into the torque wire 101. In some embodiment the torque wire 101 slidably receives the optic fiber 103. The fiber and torque can be attached or fixed through various compounds and configurations. The molded lens 104 is attached to the optical fiber 103 by an optical adhesive or other attachment mechanism.

The imaging core assembly 100 further includes an outer tube 105. In some embodiments, the outer tube 105 includes Polyethylene terephthalate (PET). The outer tube can be fabricated to have walls of varying thickness. In other embodiments, the outer tube 105 includes any suitable material, such as, but not limited to nylon, PET, co-extruder materials, jackets, bi-layer materials, tri-layer materials, silicone, siloxane-based materials, resins, and other materials suitable for use in medical devices and for in vivo applications. The outer tube can be replaced by a coating or cover in some embodiments. In one embodiment, the outer tube is disposed such that it straddles or otherwise covers a weld such as a butt weld or butt joint used to attach the torque wire and the marker band.

In some embodiments, the molded lens 104 with an optic fiber 103 bonded to it may be encased in a glue 106. In some embodiments, the glue 106 may be an UV-cured adhesive. In other embodiments, the glue 106 includes any suitable material, such as, but not limited to optical potting materials and other glues, resins or suitable adhesives. Shrink wrap assemblies and heat curable compounds can also be used to adhere or otherwise bond components described and depicted connected to or attached to each other throughout the disclosure.

The outer tube 105 may be used as a mold for the glue 106 for the molded lens 104. In some embodiments, the glue 106 is wicked into the outer tube 105, and then cured. Once cured, the end of the potting glue 106 may be cut to a desired length, or it may be left as it is. In some embodiments, the outer tube 105 that served as the mold for the glue 106 may be left on. In other embodiments, the outer tube 105 may be removed.

The outer diameter 108 of the imaging core assembly 100 is less than the outer diameter 308 of an imaging core assembly that includes a marker band 102 that are on the outside of the torque wire 101. In one embodiment, marker band 102 is a dual marker band.

FIG. 2 depicts one embodiment of the imaging core assembly 200 with a torque wire 201 that includes a beveled end 207. This bevel end 207 can be formed by an angle w. The imaging core assembly 200 includes a marker band 202 connected to a torque wire 201. The marker band 202 is configured on the inner diameter 209 of the imaging core assembly 200 in order to minimize NURD. The imaging core assembly 200 includes an optical fiber 203 bonded to a molded lens 204. In one embodiment, the molded lens 204 sits partially in the marker band 202, with the area of interest being outside of the marker band 202 to allow for imaging. In other embodiments, there is space between the marker band 202 and the molded lens 204.

In one embodiment, the imaging core assembly 200 includes an outer tube 205. In some embodiments, the outer tube 205 includes a thin-walled PET. In other embodiments, the outer tube 205 includes any suitable material, such as, but not limited to nylon, PET, co-extruder materials, jackets, bi-layer materials, tri-layer materials, silicone, siloxane-based materials, resins, and other materials suitable for use in medical devices and for in vivo applications. The outer tube 205 may be used as a mold for the potting glue 206 for the molded lens 204. In some embodiments, the glue 206 may be an UV-cured adhesive.

In other embodiments, the glue 206 includes any suitable material, such as, but not limited to lens potting material, heat curable materials, polymers, resins and other suitable adhesives and bonding compounds. In some embodiments, the potting glue 206 is wicked into the outer tube 205, and then cured. Once cured, the end of the potting glue 206 may be cut to a desired length, or it may be left as it is. In some embodiments, the outer tube 205 that served as the mold for the potting glue 206 may be left on. In other embodiments, the outer tube 205 may be removed. Typically, in various embodiments, the outer tube 205 is the same as the jacket 112.

In the embodiment of FIG. 2, the stiff section 210 and outer diameter 208 of the imaging core assembly 200 is minimized. In one embodiment, the outer diameter corresponds to the jacket 112 which extends over the lens and marker band and part of the torque wire 207. The minimization of these two features serves to reduce NURD caused by tight environments in the lumen due to either tight lesions or tortuous anatomy. In this embodiment of the imaging core assembly 200, the angularity of imaging core assembly 200 relative to the catheter is closer to zero, thereby reducing NURD.

FIG. 3A illustrates an imaging core assembly 300 that includes a torque wire 301 with L-grind detail 308. The imaging core assembly 300 includes a marker band 302 joined or otherwise connected to a torque wire 301. In various embodiments, the torque wire and the marker band are joined by a weld or other mechanism to form a joint. The marker band 302 is configured on the inner diameter 309 of the imaging core assembly 300 in order to minimize NURD. The imaging core assembly 300 includes an optic fiber 303 bonded to a molded lens 304. In one embodiment, the marker band 302 is welded 307 to the torque wire 301. This can be accomplished using a butt weld also referred to as a butt joint. In other embodiments, the marker band 302 and the torque wire 201 are connected by other means, such as, but not limited to, an adhesive material, welds, splices, joints, hinges, compression fit, internal couplers and linkages, and other devices and compounds.

The imaging core assembly 300 includes an outer tube 305. This may correspond to jacket 112 in various embodiments. In some embodiments, the outer tube 305 includes a thin-walled PET, nylon, silicone or other material. In other embodiments, the outer tube 305 includes any suitable material. The outer tube 305 may be used as a mold for the potting glue 306 for the molded lens 304. In some embodiments, the potting glue 306 may be an UV-cured adhesive or other adhesive or bonding compound as described herein or suitable for a given application. In some embodiments, the potting glue 306 is wicked into the outer tube 305, and then cured. Once cured, the end of the potting glue 306 may be cut to a desired length, or it may be left as it is. In some embodiments, the outer tube 305 that served as the mold for the potting glue 306 may be left on. In other embodiments, the outer tube 305 may be removed. The jacket 112 is part of the probe for various embodiments and positioned to overlap with joint between torque wire and marker band.

In the embodiment of FIG. 3A, the stiff section 310 and outer diameter 311 of the imaging core assembly 300 is minimized. In one embodiment, the stiff section 310 extends to end of L grind on left side of figure. The minimization of these two features serves to reduce NURD caused by tight environments in the lumen due to either tight lesions or tortuous anatomy. In this embodiment of the imaging core assembly 300, the angularity of imaging core assembly 300 relative to the catheter is closer to zero, thereby reducing NURD.

Figure 3B:
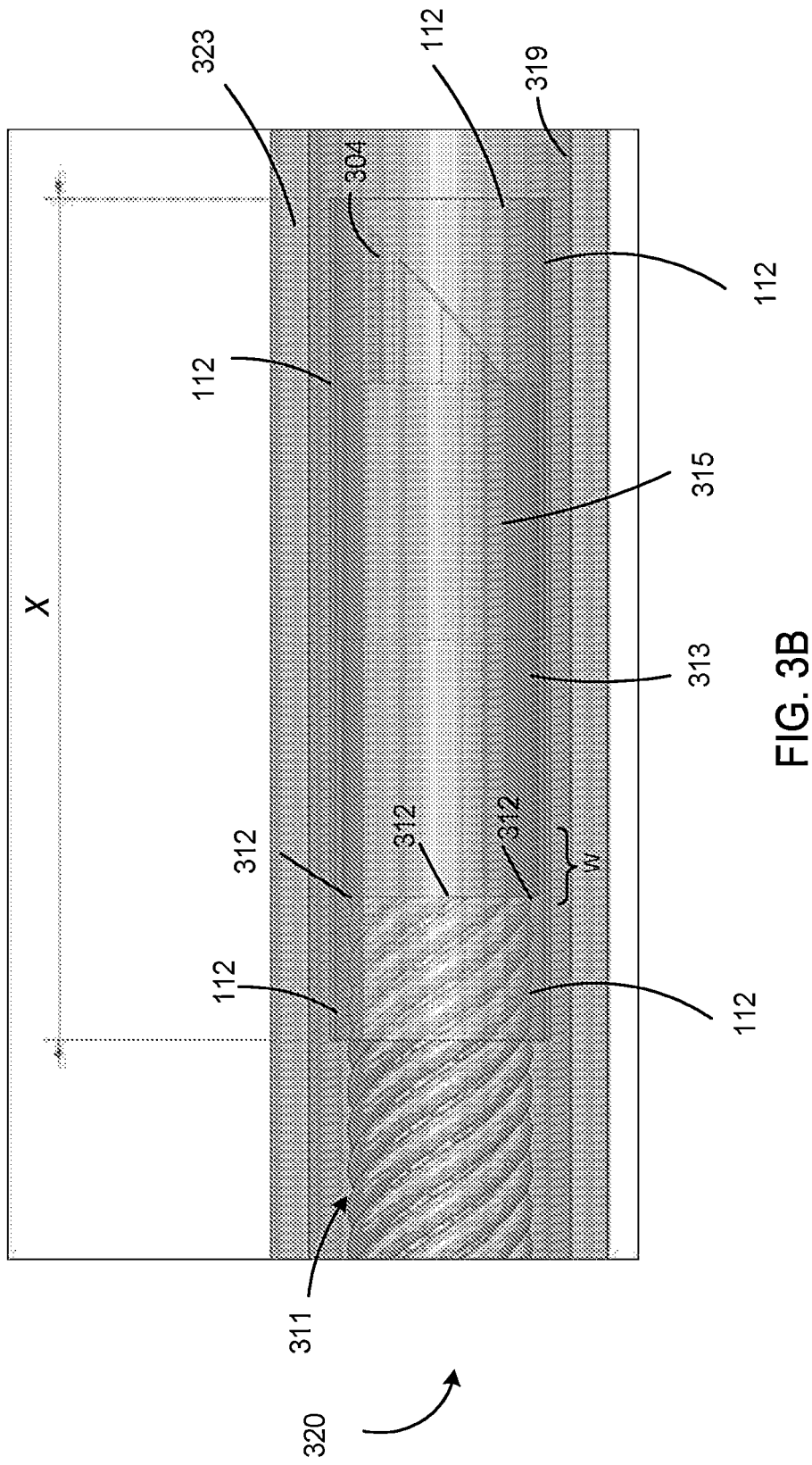
FIG. 3B is a side view of a rendering that illustrates an imaging core assembly that includes a torque wire with a butt weld joint according to an illustrative embodiment of the disclosure.

FIG. 3B depicts another embodiment of the imaging core assembly 320 with a torque wire 311 that includes a joint 312 by which it is connected to marker band 313. Jacket 312 overlaps joint 312. The imaging core assembly 320 and the torque wire can be disposed in a delivery catheter 323. The joint 312 is typically a butt weld or butt joint. In one embodiment, the joint 312 is formed by placing the torque wire 311 and the marker band 313 together, whether end to end or one nested inside the other, and welding the two metal components to form a butt weld/butt joint. FIG. 3C shows a similar embodiment 350. An optical fiber 321, as shown in FIGS. 3C and 3I), is disposed in the bore of torque wire 311 and terminates in a lens 304. Lens 304 is a molded or thermo-formed lens in one embodiment. The lens 304 can be secured by adhesive 315. Adhesive 315 can be an optical potting material in one embodiment Other suitable adhesives 315 that do not interfere with optical properties of lens 304 may be used. The lens 304 can include a channel or trough or bore to receive the fiber 312. The fiber 312 ends into the torque wire bore.

FIG. 3C is a cross-sectional view of a data collection probe imaging assembly 350 in which a molded lens 304 is shown attached to an optical fiber 321. The imaging assembly include a torque wire 311 and weld or joint 318 which can be a butt weld. The weld or joint 318 can have a width w. Adhesive 315 can be disposed with jacket 312 as shown. The optical fiber is typically first glued to lens 304 as shown in FIG. 3D. This assembly can be slid into marker band 313. The jacket 112 spans the weld 318, which can be a butt weld or butt joint between marker band 313 and torque wire 311. It is desirable to have jacket 112 positioned such that it overlaps the weld or joint 318 between torque wire 311 and marker band 313.

FIG. 3E is a top view of the data collection probe of FIG. 3D in which a molded lens is shown attached to an optical fiber. In FIG. 3D, the jacket 112 is not present nor are the other elements of FIG. 3C. The adhesive 315 shown in FIGS. 3D and 3E can be applied to attach the optical fiber to the molded lens 304. This can be the same adhesive used as shown in FIG. 3C by which additional adhesive 315 is disposed in jacket 312 and relative to the marker band 313.

With regard to FIGS. 3B and 3C, in one embodiment, the torque wire is disposed inside the marker band and the joint 312, 318 is formed between the marker band and the torque wire. In one embodiment, the torque wire is welded to the marker band and the joint 312, 318 is formed between the marker band and the torque wire. The joint 312 can have an associated with w, which is less than the length of the marker band. The imaging core assembly 320 includes a marker band 313 connected to the torque wire 311 through the joint 312, 318. Similar to FIG. 3A, the marker band 313 is configured on the inner diameter 319 of the imaging core assembly 320 in order to minimize NURD. This inner diameter is that of jacket 112 in various embodiments. This jacket 112 can be PET tube or other polymer material in various embodiments.

Figure 8A:
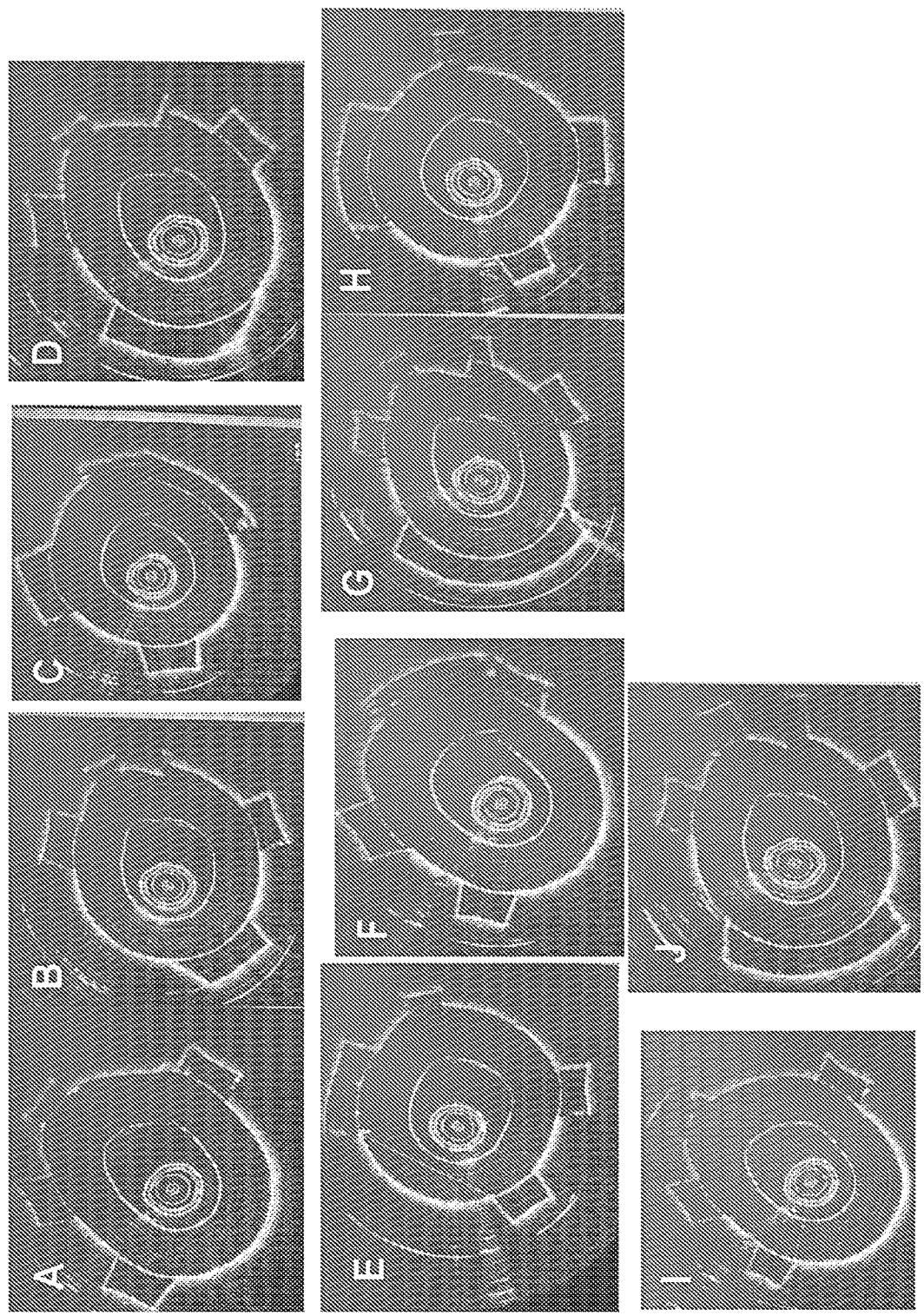
FIG. 8A is a series of OCT image frames (frame A to frame J) obtained using an OCT imaging probe and an OCT imaging system in which a first level of chatter is present during imaging.

With regard to FIGS. 3B and 3C, the welding of the torque wire 311 using a butt joint can reduce NURD, which can in turn reduce chatter. Additional details relating to chatter and NURD reduction are discussed herein including with regard to FIGS. 8A and 8B below. In general, the design feature discussed herein reduces NURD to at least below the levels that create a high level of chatter such as shown in FIG. 8A. In some embodiments, the distance x shown in FIG. 3A may be of any variable length. In some embodiments, the distance x ranges from about 0.050 mm to about 2.500 mm.

FIG. 3C and related FIGS. 3D and 3E show another embodiment of the imaging core assembly 350 with a torque wire 311 that includes a joint 318 by which it is connected to marker band 313. The use of the jacket 112 and positioning it relative to a butt weld or other joint 312 formed relative to torque wire and marker band can also help stabilize probe and reduce NURD. As shown in FIG. 3C, a torque wire 311 is butt welded to marker band 313. Jacket 112 surrounds the various elements, including a portion of the torque wire 311 which abuts marker band 313. The weld 318 can be a flush weld from torque wire 311 to the end of the marker band 313. Alternatively, the one of the two metal elements can be disposed within the other or the weld can have a width w, which applies in the flush arrangement or if one element id disposed in the other.

Figure 4A:
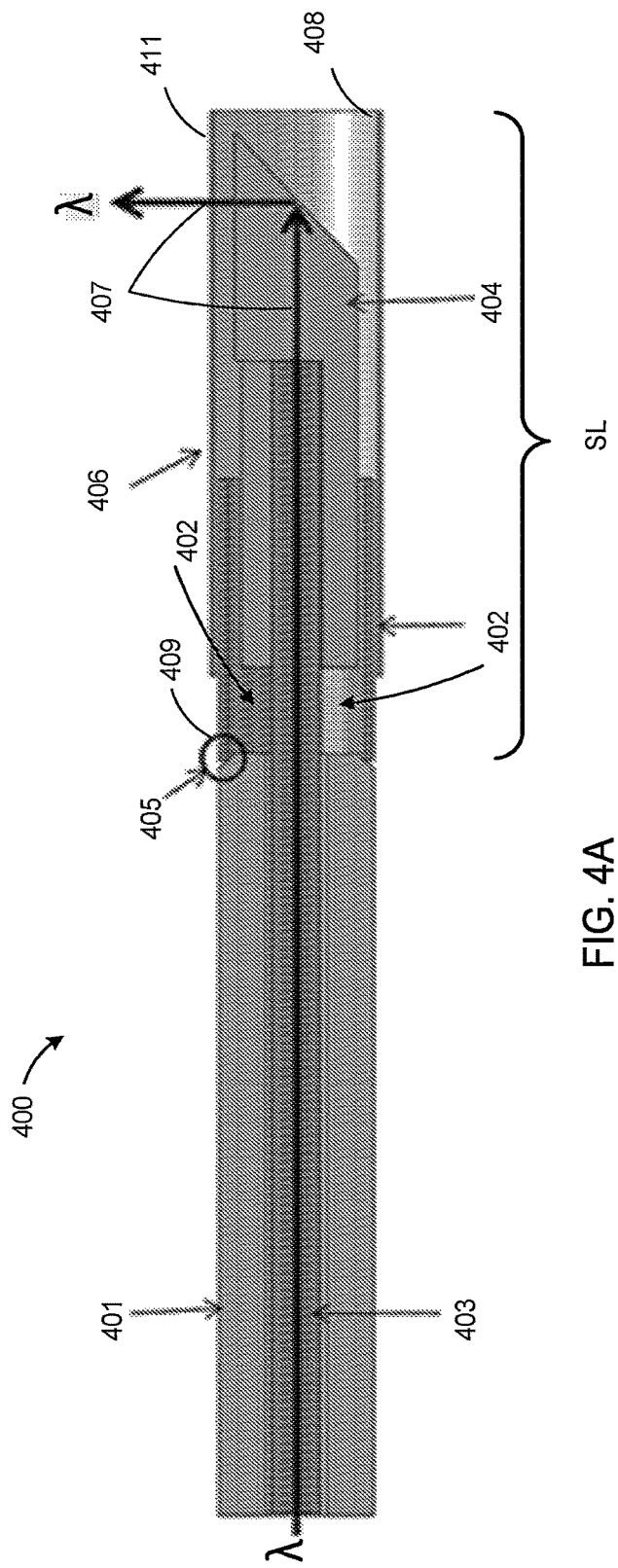
FIG. 4A is a schematic diagram that illustrates an imaging core assembly that includes a torque wire and marker band that are welded or otherwise attached or hinged together according to an illustrative embodiment of the disclosure.
Figure 4B:
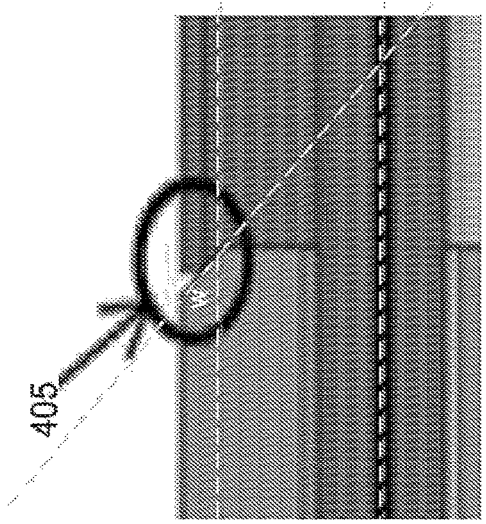
FIG. 4B is a zoomed in view of FIG. 4A showing bevel angle w according to an illustrative embodiment of the disclosure.

FIG. 4A illustrates an imaging core assembly 400 that includes a torque wire 401 and marker band 402 that are welded 405 together. A bevel formed at an angle w shown relative to horizontal axis of fiber and line along bevel (both dotted lines) is shown zoomed in in FIG. 4B. Light or electromagnetic radiation λ is shown propagating in the optical fiber and subsequently exiting the lens. The marker band 402 is configured on the inner diameter 408 of the imaging core assembly 400 in order to minimize NURD. The imaging core assembly 400 includes an optic fiber 403 bonded to a molded lens 404. In one embodiment, the marker band 402 is welded 405 to the torque wire 401. In other embodiments, the marker band 402 and the torque wire 401 are connected by other means, such as, but not limited to, an adhesive material, welds, splices, joints, hinges, compression fit, internal couplers and linkages, and other devices and compounds.

In one embodiment, the marker band 402 may be welded directly 409 to the torque wire 401. In other embodiments, the marker band 402 may be spaced away from the torque wire 401 by a gap. The imaging core assembly 400 includes a jacket 406 configured around the molded lens 404. In some embodiments, the jacket 406 includes a thin-walled PET tube or cover. FIG. 4A shows a bevel angle formed at the weld 405 between the marker band and the torque wire. The bevel angle can ranges from about 20 degrees to about 60 degrees in one embodiment.

In other embodiments, the jacket 406 includes any suitable material, such as, but not limited to polymers, PET, silicon, nylon, resins, and other polymer-based materials described herein or otherwise suitable for use as a jacket. The jacket 406 may be used as a mold for the potting glue for the molded lens 404. In some embodiments, the molded lens 404 directs light along a perpendicular light path 407. In other embodiments, the molded lens 404 may direct light along a light path 407 at any suitable angle. In some embodiments, the jacket 406 may be left on. In other embodiments, the jacket 406 may be removed. In one embodiment, the use of the lens with an imaging assembly results in one or more of: improved beam imaging, brighter images, improved resolution of external elastic lamina (EEL) measurements, and improved stent strut resolution.

In the embodiment of FIG. 4A, an exemplary stiff section having section length SL is shown. In this embodiment, the outer diameter 411 of the imaging core assembly 400 is minimized. The minimization of these two features serves to reduce NURD caused by tight environments in the lumen due to either tight lesions or tortuous anatomy. In this embodiment of the imaging core assembly 400, the angularity of imaging core assembly relative to the catheter is closer to zero, thereby reducing NURD.

Figure 5:
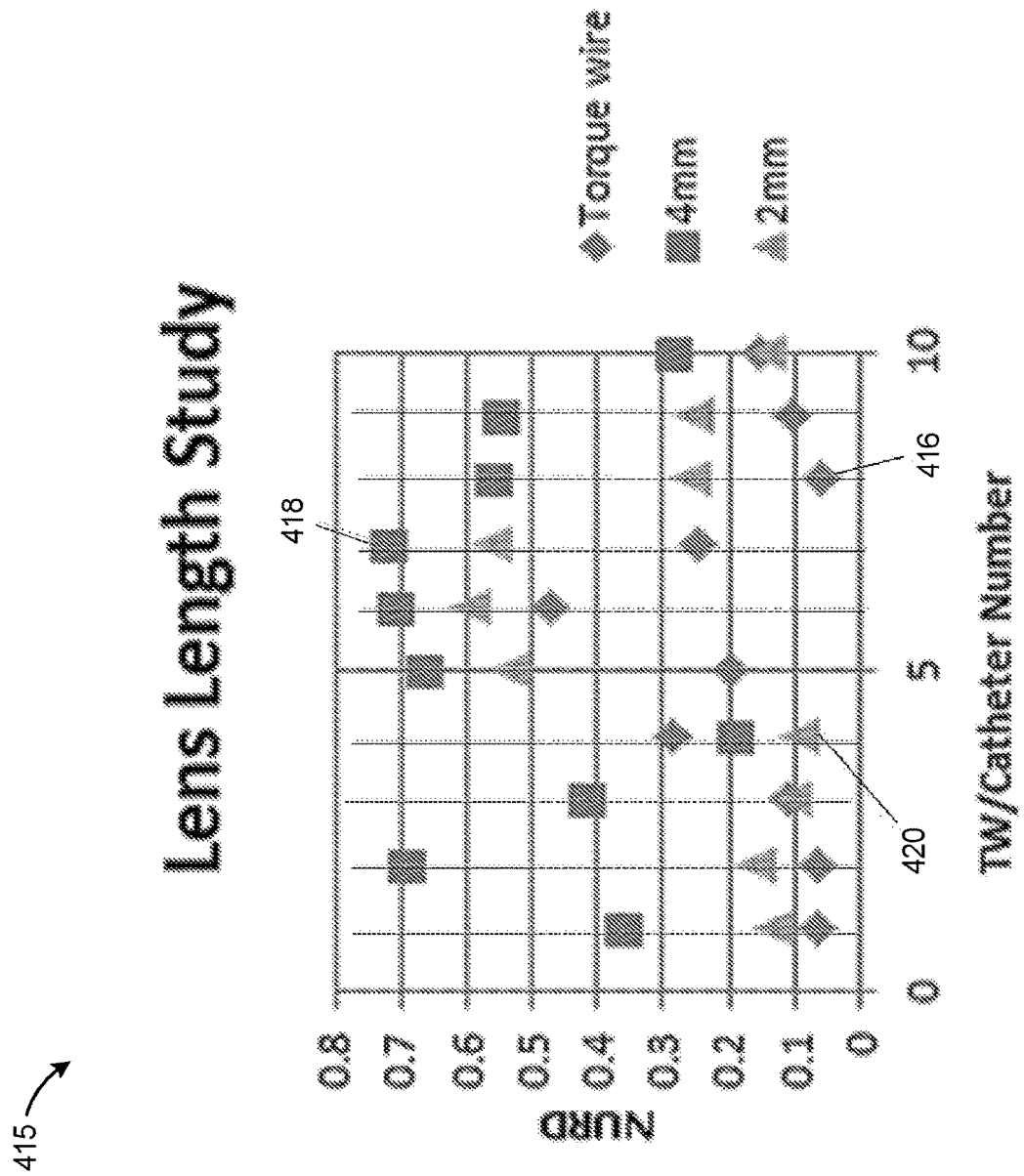
FIG. 5 is a plot of the NURD in catheters based on the length of the relevant section and other parameters according to an illustrative embodiment of the disclosure.

FIG. 5 is a plot of NURD values (y-axis) versus torque (TW)/catheter number. The diamond (416) shows torque wire (TW) values plotted versus 4 mm values (418), which are shown by squares and 2 mm values (420), which are shown by triangles. The 2 mm and 4 mm values correspond to lens length such as the unitary lens or other lens using the imaging assembly. The torque wire values provide a baseline as there is no lens on a bare torque wire, and thus the effective lens length when just the torque wire is considered is zero.

As shown in plot 415 of FIG. 5, along the vertical columns (doted vertical lines), which include a torque wire value, a 2 mm lens length value, and a 4 mm lens length value. The 4 mm lens length value is the top point in each column and thus corresponding to the higher NURD values. The 2 mm lens length values are below the 4 mm values and the torque wire points are the lowest point in the column or points that overlap with the 2 mm lens length. This plot 415 illustrates the benefit of reducing the lens length from 4 mm to 2 mm (and other reduced values) which corresponds to reducing the stiff section length for various probe embodiments. As noted herein, by disposing a portion of the lens length within the marker band, the stiff lens and stiff marker band overlap and thereby from such overlapping the overall stiff section length is reduced. As shown, the length reduction in one or more of the foregoing stiff sections or other section beneficially reduces NURD.

Figure 6:
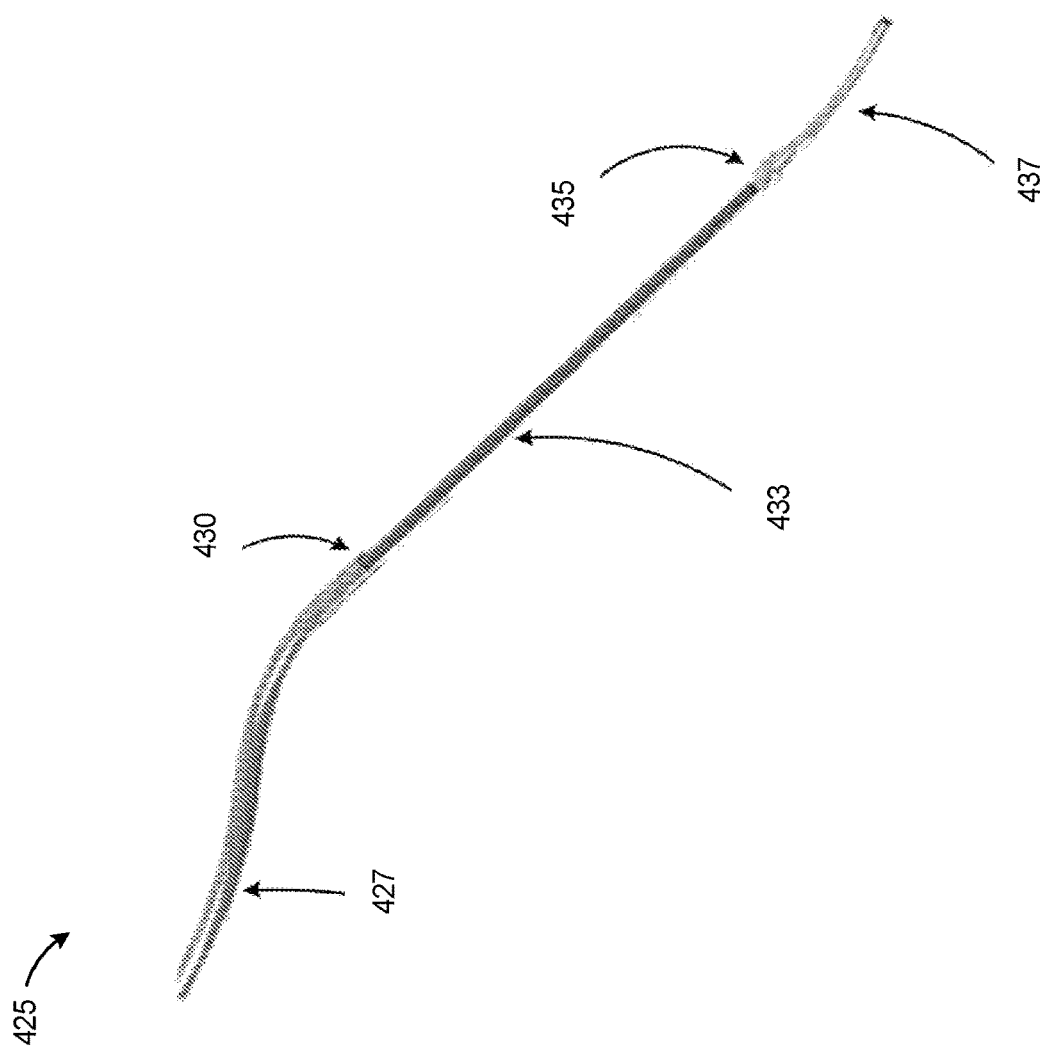
FIG. 6 is a perspective view that illustrates a catheter with an imaging core assembly according to an illustrative embodiment of the disclosure.

FIG. 6 is a perspective view of a catheter 425 suitable for receiving a probe embodiment as disclosed herein. The catheter is as rapid exchange (RX) catheter in one embodiment. Accordingly, a probe that includes a torque wire, a lens, and a marker band as well as optionally other components can be inserted within the catheter 425 and rotated such that data such as image data can be collected by the rotating imaging assembly. The imaging occurs over a pullback region that tracks the imaging window shown in the middle of the catheter 425. As shown in FIG. 6 and in FIGS. 7A-7C, the catheter includes a braided shaft 427 which undergoes a transition through a reduced transition area 430 to an imaging window 433. An input port 453 is also present. The imaging window continues until it reaches an improved RX rail 435 and the distal tip 437 includes a reduced RX profile. As shown, in FIG. 7B, the catheter includes a proximal shaft, which connects to the window tube, which in turn connects to a distal assembly which is shown in FIG. 7A.

In one embodiment, the probe is of a singular construction or integral such that its components or subassemblies are all a common material such as a molded polymer or metal. In some embodiment, two or more of the components of a probe or catheter can be different materials or manufactured using different processes and at different points in time. In some embodiments, a data collection probe includes two or more of the following components, a lens, a torque wire, a hinge, a joint, an annular ring or band that includes a radiopaque material, a weld, an adhesive, potting material, a tube, a sheath, a jacket, and an optical fiber.

As discussed herein, the disclosure is directed to improving upon various imaging and data collection probe designs. In particular, various embodiments were designed to mitigate the effect of NURD and other phenomena associated with it. Chatter is one such related undesirable effect. Chatter occurs as a result of high levels of NURD. Specifically, chatter occurs when an image frame displays more or less than 360 degrees of rotation. For example, a chatter frame may only have 300 degrees of rotation or it could have 400 degrees of rotation, both of which are undesirable. In part, the use of various joints, joins, welds, and the selection of stiff sections and the lengths associated therewith help reduce chatter and NURD in various embodiments.

Chatter occurs when NURD reaches high levels such that the catheter does not rotate 360 degrees in every frame. Therefore, chatter is an extreme case of NURD. Chatter may be measured by how many degrees are displayed in a frame. For example, the greater deviation from 360 degrees, the worse the chatter. On such a scale, a one level of chatter may be distinguished from a one level of chatter. For example, for one image, one level of chatter may be in the range of ±10 degrees from 360 degrees of rotation and a second level of chatter may be any value greater than that.

Figure 8B:
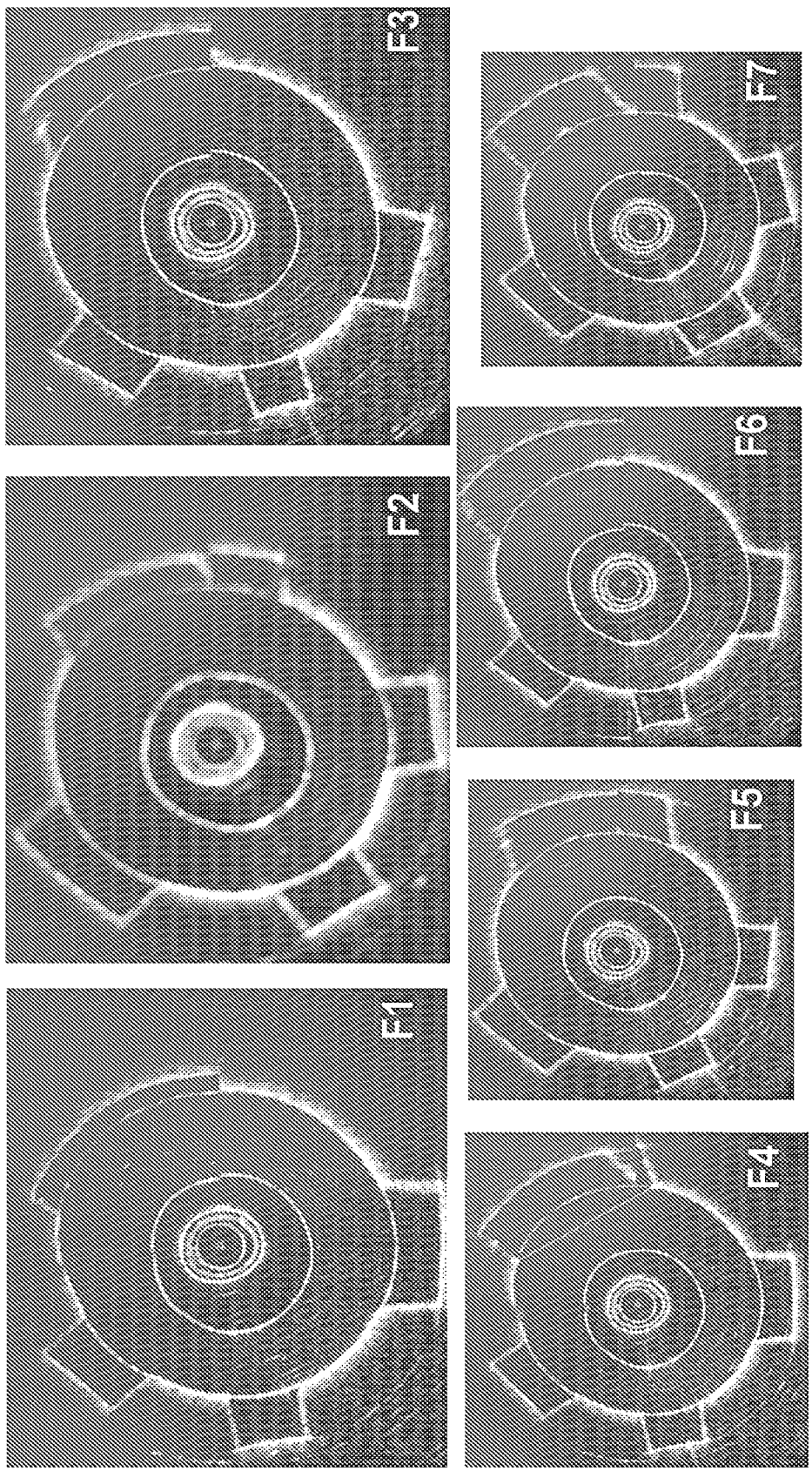
FIG. 8B is a series of OCT image frames (frame F1 to frame F7) obtained using an OCT imaging probe and an OCT imaging system in which a second level of chatter is present during imaging, wherein the second level of chatter is less than the first level of chatter.

FIG. 8A illustrates a series of frames (frame A to frame J) obtained using an OCT imaging probe and an OCT imaging system. The OCT probe was used in an experimental environment designed to permit rotation and imaging by the probe. A frame-by-frame progression of chatter when there is a first level of chatter is shown in the images from the rotating probe. As seen in frames A-J, the first level of chatter significantly distorts the resulting image and is undesirable. FIG. 8B illustrates a frame-by-frame progression of a probe that includes the stiffness section length reduction. The image frames in FIG. 8B, also are for a probe with butt weld in which the jacket spans the weld. As seen in frames F1-F7, the distortion is less than the first level of chatter shown in FIG. 8A. In light of this, the design improvements discussed herein show benefits in terms of reduce chatter and thus reducing NURD.

More generally, as used herein, the term unitary construction or unitary encompasses embodiments that are of a singular construction as well as embodiments in two parts of combined to form an assembly or combination. As noted above, in other embodiments, the term "unitary" can also refer to an object that is a single piece. For example, an object formed from a single injection molding, e.g., without assembly or addition of further parts can be described as unitary or having a unitary structure.

Although the preceding and following text sets forth a detailed description of different embodiments of the disclosure, it should be understood that the legal scope of the disclosure is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed invention.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the terms "about" or "approximately" are before a quantitative value, the present teachings also include the specific quantitative value itself, unless specifically stated otherwise. As used herein, the term "about" refers to a ±10% variation from the nominal value. As used herein, the term "approximately" refers to a ±10% variation from the nominal value. As used herein, the term "substantially" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

The invention claimed is:

1. An intravascular data collection probe comprising:
a marker band defining a bore;
a lens defining a beam directing surface, wherein the lens is spaced from the marker band;
an optical fiber extending through the bore of the marker band and having a terminal end optically coupled to the lens, wherein a portion of the lens and a portion of the optical fiber overlap with each other in a single plane; and
a jacket defining a jacket bore, wherein the marker band, the lens, and a section of the optical fiber are disposed in the jacket bore such that the jacket surrounds the marker band, the lens, and a section of the optical fiber.

2. The probe of claim 1, wherein an end face of the lens is disposed within the bore of the marker band and the beam directing surface extends past a distal end of the marker band.

3. The probe of claim 1, further comprising a coating, the coating is disposed on or relative to the lens such that the lens and the coating define a compound lens system.

4. The probe of claim 1 wherein the marker band is substantially cylindrical.

5. The probe of claim 1 wherein the lens is a molded unitary lens defining a trough having a fiber section length and the beam directing surface, wherein the trough is an elongate optical fiber receiving section.

6. The probe of claim 1 further comprising a torque wire defining a torque wire bore, a first end and a second end.

7. The probe of claim 6, wherein the optical fiber extending through the marker band is disposed in the torque wire bore.

8. The probe of claim 6, wherein the marker band is joined to a torque wire end face.

9. The probe of claim 8, wherein the marker band is joined to the torque wire end face by a butt weld.

10. The probe of claim 6, wherein the torque wire end face is disposed in the jacket bore.

11. The probe of claim 6, wherein the torque wire has a first stiffness, wherein the marker band has a second stiffness greater than the first stiffness, wherein a sum of length of marker band and length of lens extending from marker band defines a stiffness section.

12. The probe of claim 11, wherein the probe is configured to reduce chatter when rotating the probe and collecting image data.

13. The probe of claim 8, wherein the torque wire end face defines a bevel oriented at a bevel angle relative to a longitudinal axis of the torque wire bore, wherein the end face is welded to the marker band.

14. The probe of claim 13 wherein the bevel angle ranges from about 20 degrees to about 60 degrees.

15. The probe of claim 6, wherein the torque wire defines a first outer diameter and a second outer diameter, wherein the second outer diameter is less than the first outer diameter.

16. The probe of claim 15, wherein the second outer diameter spans a distance from the second end of the torque wire until the second outer diameter reaches a step up to the first outer diameter.

17. The probe of claim 15, wherein a portion of the second end of the torque wire that defines the second outer diameter is disposed within the bore of the marker band.

18. The probe of claim 6, wherein the torque wire is connected to the marker band by a joint substantially in a single plane.

19. The probe of claim 6, wherein the torque wire is connected to the marker band by a flexible joint.

20. The probe of claim 1, wherein the jacket substantially is cylindrical and extends around an outer perimeter of the probe.

* * * * *